US009469605B2

(12) United States Patent
Snow et al.

(10) Patent No.: US 9,469,605 B2
(45) Date of Patent: *Oct. 18, 2016

(54) COMPOUNDS AND COMPOSITIONS FOR USE A MODULATORS OF TAU AGGREGATION AND ALLEVIATION OF TAUOPATHIES

(71) Applicant: PROTAMED, INC., Kirkland, WA (US)

(72) Inventors: Alan D Snow, Lynnwood, WA (US); Qubai Hu, Kirkland, WA (US); Thomas Lake, Snohomish, WA (US); Judy Cam, Bellevue, WA (US)

(73) Assignee: PROTAMED, INC., Kirkland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/300,572

(22) Filed: Jun. 10, 2014

(65) Prior Publication Data

US 2014/0288183 A1    Sep. 25, 2014

Related U.S. Application Data

(60) Division of application No. 13/868,291, filed on Jul. 18, 2013, now abandoned, which is a division of application No. 13/010,023, filed on Jan. 20, 2011, now Pat. No. 8,455,687, which is a continuation-in-part of application No. 12/269,017, filed on Nov. 11, 2008, now abandoned, which is a continuation of application No. 10/452,851, filed on May 30, 2003, now Pat. No. 7,514,583, said application No. 13/868,291 is a continuation-in-part of application No. 12/244,968, filed on Oct. 3, 2008, now Pat. No. 8,829,198.

(60) Provisional application No. 60/385,144, filed on May 31, 2002, provisional application No. 60/409,100, filed on Sep. 9, 2002, provisional application No. 60/412,272, filed on Sep. 20, 2002, provisional application No. 60/435,880, filed on Dec. 20, 2002, provisional application No. 61/001,441, filed on Oct. 31, 2007, provisional application No. 61/299,005, filed on Jan. 28, 2010, provisional application No. 60/463,104, filed on Apr. 14, 2003.

(51) Int. Cl.
| | |
|---|---|
| C07C 235/56 | (2006.01) |
| C07C 275/34 | (2006.01) |
| A61K 31/167 | (2006.01) |
| A61K 31/17 | (2006.01) |
| C07C 311/29 | (2006.01) |
| C07C 235/38 | (2006.01) |
| C07C 237/22 | (2006.01) |
| A61K 31/05 | (2006.01) |
| A61K 31/164 | (2006.01) |
| A61K 31/18 | (2006.01) |
| A61K 31/415 | (2006.01) |
| A61K 31/4196 | (2006.01) |
| C07D 249/08 | (2006.01) |
| C07C 307/10 | (2006.01) |
| C07D 235/00 | (2006.01) |
| C07C 69/84 | (2006.01) |
| C07C 237/40 | (2006.01) |

(52) U.S. Cl.
CPC ............ *C07C 311/29* (2013.01); *A61K 31/05* (2013.01); *A61K 31/164* (2013.01); *A61K 31/167* (2013.01); *A61K 31/18* (2013.01); *A61K 31/415* (2013.01); *A61K 31/4196* (2013.01); *C07C 69/84* (2013.01); *C07C 235/38* (2013.01); *C07C 237/22* (2013.01); *C07C 237/40* (2013.01); *C07C 275/34* (2013.01); *C07C 307/10* (2013.01); *C07D 235/00* (2013.01); *C07D 249/08* (2013.01)

(58) Field of Classification Search
None
See application file for complete search history.

(56) References Cited

U.S. PATENT DOCUMENTS 5,166,180 A    11/1992  Jenkins
7,514,583 B2 *  4/2009  Snow et al. .................. 564/179

FOREIGN PATENT DOCUMENTS

EP          324521          7/1989

OTHER PUBLICATIONS

Database CAPLUS in STN, Acc. No. 1966:484808, Leader et al., Biochemical Pharmacology (1966), 15(9), pp. 1379-1387 (abstract).*
Database CAPLUS in STN, Acc. No. 1977:534458, Runge et al. DD 122967 A1 (Nov. 12, 1976) (abstract).*

* cited by examiner

*Primary Examiner* — Brian J Davis
(74) *Attorney, Agent, or Firm* — Techlaw LLP; Sam K. Tahmassebi

(57) ABSTRACT

This invention relates to the use of bis- and tris-dihydroxyaryl compounds as well as sulfonamides, heteroaryls, tricycloalkyl and their analogs and pharmaceutically acceptable salts, for modulating tau aggregation and alleviating tauopathies, such as Alzheimer's disease (AD), Pick's disease (PiD), progressive supranuclear palsy (PSP), corticobasal degeneration (CBD) and familial frontotemporal dementia/Parkinsonism linked to chromosome 17 (FTDP-17), amyotrophic lateral sclerosis/Parkinsonism-dementia complex, argyrophilic grain dementia, dementia pugilistic, diffuse neurofibrillary tangles with calcification, progressive subcortical gliosis and tangle only dementia.

8 Claims, No Drawings

COMPOUNDS AND COMPOSITIONS FOR USE A MODULATORS OF TAU AGGREGATION AND ALLEVIATION OF TAUOPATHIES

RELATED APPLICATIONS

This application is a divisional of U.S. application Ser. No. 13/868,291 filed Apr. 23, 2013 which is a divisional of U.S. application Ser. No. 13/010,023 filed Jan. 20, 2011 now U.S. Pat. No. 8,455,687 issued Jun. 4, 2013 and claims the benefit of priority under 35 USC. §120 to, and is a continuation in part of U.S. application Ser. No. 12/269,017 filed Nov. 11, 2008, now abandoned which is a continuation of U.S. application Ser. No. 10/452,851, filed May 30, 2003 now issued U.S. Pat. No. 7,514,583, which claimed priority under 35 USC §119(e) to:
(1) U.S. Provisional Application No. 60/385,144, filed May 31, 2002,
(2) U.S. Provisional Application No. 60/409,100, filed Sep. 9, 2002,
(3) U.S. Provisional Application No. 60/412,272, filed Sep. 20, 2002,
(4) U.S. Provisional Application No. 60/435,880, filed Dec. 20, 2002, and
(5) U.S. Provisional Application No. 60/463,104, filed Apr. 14, 2003.

U.S. application Ser. No. 13/868,291 also claims priority under 35 USC §119(e) to U.S. Provisional Application No. 61/299,005, filed Jan. 28, 2010.

U.S. application Ser. No. 13/868,291 claims the benefit of priority under 35 USC §120 to, and is a continuation in part of, U.S. application Ser. No. 12/244,968 filed Oct. 3, 2008, which claimed priority under 35 USC §119(e) to U.S. Provisional Application No. 61/001,441, filed Oct. 31, 2007.

The entire contents of all of these applications are incorporated by reference into this application.

TECHNICAL FIELD

This invention relates to the use of bis- and tris-dihydroxyaryl compounds as well as sulfonamides, heteroaryls, tricycloalkyl and their analogs and pharmaceutically acceptable esters, and pharmaceutical compositions containing them, for modulation of tau aggregation and dissolution/disruption/inhibition of tau aggregates, and alleviation of tauopathies, such as Alzheimer's disease (AD), Pick's disease (PiD), progressive supranuclear palsy (PSP), corticobasal degeneration (CBD) and familial frontotemporal dementia/Parkinsonism linked to chromosome 17 (FTDP-17), amyotrophic lateral sclerosis/Parkinsonism-dementia complex, argyrophilic grain dementia, dementia pugilistic, diffuse neurofibrillary tangles with calcification, progressive subcortical gliosis and tangle only dementia.

BACKGROUND OF THE INVENTION

Tau is a microtubule associated protein found primarily in neuronal axons. Physiological phosphorylation of tau regulates the dynamics of the association of tau with tubulin, and thereby microtubule stability (Mazanetz. M. P. and Fischer, P. M. 2007. Nature Reviews 6:464-479). The stabilization of the microtubules in axons ensures that maintain their function for axonal transport, growth and branching (Bulic, B et al., 2009 Angew. Chem. Int. Ed. 48:2-15). Hyperphosphorylation and misfolding of the tau protein is thought to be the causative factor in abnormal intracellular aggregation leading ultimately to neuronal dysfunction. Protein aggregates have been found to be toxic to neurons.

Abnormal intraneuronal tau aggregation has three basic pathological manifestations; neurofibrillary tangles (NFT's), neuropil threads (NT's) and the argyrophilic dystrophic neurite plaques (Braak, H and Braak, E, Neurobio. of Aging. 1997 18(4):351-357). Structurally, the NFT's are principally comprised of paired helical filaments (PHF) comprised of two filamentous tau proteins twisted around one another with a crossover repeat of 80 nm and a width of 8-20 nm (Li, D., et al., 2008. Computational Biology 4(12) and Kidd, M 1963 Nature, 197:192). There are six stages (Braak stages I-VI) of tau deposition in the brain, which progress temporally at defined anatomical locations with the initial stages characterized primarily by the deposition of NFT's and NT's and the secondary stages further accompanied by NP (Braak, 1997). In AD and other neuropathies, Braak's stages correlate well with clinical disease progression as demonstrated by increasing cognitive dysfunction. Severe cortical destruction which occurs around stages III-IV coincides with the first manifestations of the clinical onset of AD. Although no tau mutations have been identified in AD there is a strong correlation between NFT density and cognitive decline in AD (Brunden, K. R., Trojanowski, J. Q., and Lee, V. M. 2009 Nature Reviews 8:783-93).

New biomarkers and models of their temporal characteristics are becoming even more useful for the diagnosis and characterization of AD (Jack et al., 2010. Lancet 9:119-28). Specifically, tau deposition is associated with neurodegeneration in AD and an increase in CSF tau is an important indicator of tau pathologic changes and correlates well with clinical disease severity. A decrease in FDG-PET correlates well with increased CSF tau and both are valid indicators of synaptic dysfunction (Jack et al, ibid). This model of biomarker ordering, especially in mildly cognitive impaired individuals, has important implications for clinical trials. Potential therapeutics could be more accurately assessed for efficacy is they are able to change the trajectory of cognitive deterioration and individuals might be more selectively chosen for trials (Jack et al, ibid).

Tau hyperphosphorylation is a common characteristic of a number of dementing disorders collectively known as tauopathies, some of which have disctinct tau pathology combined with other brain pathologies. Tauopathies include Alzheimer's disease (AD), Pick's disease (PiD), progressive supranuclear palsy (PSP), corticobasal degeneration (CBD) and familial frontotemporal dementia/Parkinsonism linked to chromosome 17 (FTDP-17), amyotrophic lateral sclerosis/Parkinsonism-dementia complex, argyrophilic grain dementia, dementia pugilistic, diffuse neurofibrillary tangles with calcification, progressive subcortical gliosis and tangle only dementia. (Spillantini, M G and Goedert M, 1998 Trends Neurosci. October 21(10):428-33). In AD, tau pathology is typically limited to the neurons while other tauopathies can pathologically exhibit both neuronal and glial tau deposition (Higuchi, M, et al., 2002. Neuropsychopharmacology: The Fifth Generation of Progress, Chapter 94: Tau protein and tauopathy).

It has recently been postulated that tau protein may link Parkinson's and Alzheimer's disease (Shulman, J. M. and DeJager, P. L. 2009 Nature Genetics 41(12): 1261-1262). This study examined whether any genome wide association occurs between the two diseases and found that three genes and two new loci were linked to increased susceptibility.

It is presently not known if tau is a causative factor in disease but it is likely that either a loss or gain for function results in pathology. In FTLD17, a missense mutation affects the alternative splicing of tau resulting in the disruption of the ratio of the 4R to 3R tau isoform. More of the 4R isoform with an extra repeat of the microtubule binding region may lead to overstabilization of the microtubules resulting in disease. Other post-translational events such as alterations in kinase activity and glycosylation could also cause hyperphosphorylation and result in disease or alternatively proteolytic cleavage could produce truncated tau products more inclined to aggregate (Brunden, ibid).

Recently tau toxicity has been re-emphasized as an important therapeutic target in neurodegerative tauopathies (Keystone Symposium, March 2009). Routes for developing therapeutics are either directed to inhibiting tau-phosphorylation kinases or seeking compounds effective in the modulation of tau aggregation and/or the dissolution or disruption of tau aggregates which may prove equally useful or more specific for the alleviation of tauopathies (Rafii, M. and Aisen, P. 2009 BMC Medicine 7:7). A recent paper surveyed the efficacy of several classes of compounds for their ability to prevent tau aggregation and disaggregate pre-formed tau fibrils (Bulic et al.). Although there are general concerns regarding the toxicity of disassembled fibrils, Bulic et al., were able to show that reversing tau aggregation resulted in increased cell viability.

SUMMARY OF THE INVENTION

In a first aspect, this invention is bis- and tris-dihydroxyaryl compounds and their pharmaceutically acceptable esters, and pharmaceutically acceptable salts thereof for use in the modulation of tau aggregation and dissolution/disruption/inhibition of tau aggregates.

The compounds are:
(1) compounds of the formula:

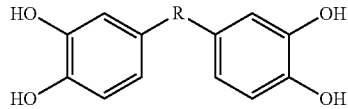

where:
R is a $C_1$-$C_{10}$ alkylene group, in which, when the number of carbon atoms is at least 2, there are optionally 1 or 2 non-adjacent double bonds; 1 to 3 non-adjacent methylene groups are optionally replaced by NR' (where R' is H, alkyl, or acyl), O, or S; and 1 or 2 methylene groups are optionally replaced by a carbonyl or hydroxymethylene group; and
(2) the compounds that are:
3,4,3',4'-tetrahydroxybenzoin (compound DC-001); 3,4,3',4'-tetrahydroxydesoxybenzoin (compound DC-002); 3,4,3',4'-tetrahydroxydiphenylmethane (compound DC-003); 1,2-bis(3,4-dihydroxyphenyl)ethane (compound DC-004); 1,3-bis(3,4-dihydroxyphenyl)propane (compound DC-005); 3,4,3',4'-tetrahydroxychalcone (compound DC-006); 3,5-bis(3,4-dihydroxyphenyl)-1-methyl-2-pyrazoline (compound DC-007); 4,6-bis(3,4-dihydroxyphenyl)-3-cyano-2-methylpyridine (compound DC-008); 1,4-bis(3,4-dihydroxybenzyl)piperazine (compound DC-009); N,N'-bis(3,4-dihydroxybenzyl)-N,N'-dimethylethylenediamine (compound DC-0010); 2,5-bis(3,4-dihydroxybenzyl)-2,5-diaza[2.2.1]bicycloheptane (compound DC-0011); N,N'-bis(3,4-dihydroxybenzyl)-trans-1,2-diaminocyclohexane (compound DC-0012); N,N'-bis(3,4-dihydroxybenzyl)-trans-1,4-diaminocyclohexane (compound DC-0013); N,N'-bis(3,4-dihydroxybenzyl)-cis-1,3-bis(aminomethyl)cyclohexane (compound DC-0014); N-(3,4-dihydroxybenzyl)proline 3,4-dihydroxybenzylamide (compound DC-0015); 2-(3,4-dihydroxybenzyl)isoquinoline-3-carboxylic acid 3,4-dihydroxyphenethylamide (compound DC-0016); 2,6-bis(3,4-dihydroxybenzyl)-cyclohexanone (compound DC-0017); 3,5-bis(3,4-dihydroxybenzyl)-1-methyl-4-piperidinone (compound DC-(0018); 2,4-bis(3,4-dihydroxybenzyl)-3-tropinone (compound DC-0019); tris-(3,4-dihydroxybenzyl)methane (compound DC-0020); α-(3,4-dihydroxybenzamido)-3,4-dihydroxycinnamic acid 3,4-dihydroxybenzyl amide (compound DC-0021); 4-(3,4-dihydroxybenzylaminomethylene)-2-(3,4-dihydroxyphenyl)oxazolin-5-one (compound DC-0022); 1,4-bis(3,4-dihydroxybenzoyl)piperazine (compound DC-0023); N,N'-bis(3,4-dihydroxybenzoyl)-N,N'-dimethylethylenediamine (compound DC-0024); 2,5-bis(3,4-dihydroxybenzoyl)-2,5-diaza[2.2.1]bicycloheptane (compound DC-0025); N,N'-bis(3,4-dihydroxybenzoyl)-trans-1,2-diaminocyclohexane (compound DC-0026); N,N'-bis(3,4-dihydroxybenzoyl)-cis-1,3-bis(aminomethyl)cyclohexane (compound DC-0027); 3,6-bis(3,4-dihydroxybenzyl)-2,5-diketopiperazine (compound DC-0028); 3,6-bis(3,4-dihydroxybenzylidene)-1,4-dimethyl-2,5-diketopiperazine (compound DC-0029); N-(3,4-dihydroxyphenylacetyl)proline 3,4-dihydroxyanilide (compound DC-0030); 2,3-bis(3,4-dihydroxyphenyl)butane (compound DC-0031); 1,3-bis(3,4-dihydroxybenzyl)benzene (compound DC-0032); 1,4-bis(3,4-dihydroxybenzyl)benzene (compound DC-0033); 2,6-bis(3,4-dihydroxybenzyl)pyridine (compound DC-0034); 2,5-bis(3,4-dihydroxybenzyl)thiophene (compound DC-0035); 2,3-bis(3,4-dihydroxybenzyl)thiophene (compound DC-0036); 1,2-bis(3,4-dihydroxyphenyl)cyclohexane (compound DC-0037); 1,4-bis(3,4-dihydroxyphenyl)cyclohexane (compound DC-0038); 3,7-bis(3,4-dihydroxyphenyl)bicyclo[3.3.0]octane (compound DC-0039); 2,3-bis(3,4-dihydroxyphenyl)-1,7,7-trimethylbicyclo[2.2.1]heptane (compound DC-0040); 1,2-bis(3,4-dihydroxyphenoxy)ethane (compound DC-0041); 1,3-bis(3,4-dihydroxyphenoxy)propane (compound DC-0042); trans-1,2-bis(3,4-dihydroxyphenoxy)-cyclopentane (compound DC-0043); N-(3,4-dihydroxybenzyl)-3-(3,4-dihydroxyphenoxy)-2-hydroxypropylamine (compound DC-0044); 3,4-dihydroxyphenoxyacetic acid 3,4-dihydroxyanilide (compound DC-0045); 3,4-dihydroxyphenoxyacetic acid 3,4-dihydroxybenzylamide (compound DC-0046); 3,4-dihydroxyphenoxyacetic acid 3,4-dihydroxyphenethylamide (compound DC-0047); 3,4-dihydroxybenzoic acid p-(3,4-dihydroxyphenoxy)anilide (compound DC-0048); 3,4-dihydroxybenzoic acid o-(3,4-dihydroxyphenoxy)anilide (compound DC-0049); 2,6-bis(3,4-dihydroxyphenoxy)pyridine (compound DC-0050), 3,4-dihydroxybenzoic acid 3,4-dihydroxyanilide (compound DC-0051); 3,4-dihydroxybenzoic acid 3,4-dihydroxybenzylamide (compound DC-0052); 3,4-dihydroxybenzoic acid 3,4-dihydroxyphenethylamide (compound DC-0053); 3,4-dihydroxyphenylacetic acid 3,4-dihydroxyanilide (compound DC-0054); 3,4-dihydroxyphenylacetic acid 3,4-dihydroxybenzylamide (compound DC-0055); 3,4-dihydroxyphenylacetic acid 3,4-dihydroxyphenethylamide (compound DC-0056); 3-(3,4-dihydroxyphenyl)propionic acid 3,4-dihydroxyanilide (compound DC-0057); 3-(3,4-dihydroxyphenyl) propionic acid 3,4-dihydroxybenzylamide (compound DC-0058); 3-(3,4-dihydroxyphenyl)propionic acid 3,4-dihydroxyphenethylamide (compound DC-0059); 3,4-dihydroxycinnamic acid 3,4-dihydroxyanilide (compound DC-0060); 3,4-dihydroxycinnamic acid 3,4-dihydroxybenzylamide (compound DC-0061); 3,4-dihydroxycinnamic acid 3,4-dihydroxyphenethylamide (compound DC-0062); oxalic acid bis(3,4-dihydroxyanilide) (compound DC-0063); oxalic acid bis(3,4-dihydroxybenzylamide) (compound DC-0064); oxalic acid bis(3,4-dihydroxyphenethylamide) (compound DC-0065); succinic acid bis(3,4-dihydroxyanilide) (compound DC-0066); succinic acid bis(3,4-dihydroxybenzylamide) (compound DC-0067); succinic acid bis(3,4-dihydroxyphenethylamide) (compound DC-0068); maleic acid bis(3,4-dihydroxyanilide) (compound DC-0069); maleic acid bis(3,4-dihydroxybenzylamide) (compound DC-0070); fumaric acid bis(3,4-dihydroxyanilide) (compound DC-0071); fumaric acid bis(3,4-dihydroxybenzylamide) (compound DC-0072); bis(3,4-dihydroxybenzyl)amine (compound DC-0073); N-(3,4-dihydroxybenzyl)-3,4-dihydroxyphenethylamine (compound DC-0074); tris(3,4-dihydroxybenzyl)amine (compound DC-0075); 1,3-bis(3,4-dihydroxyphenyl)urea (compound DC-0076); 1-(3,4-dihydroxyphenyl)-3-(3,4-dihydroxybenzyl)urea (compound DC-0077); 1-(3,4-dihydroxyphenyl)-3-(3,4-dihydroxyphenethyl)urea (compound DC-0078); 3-deoxy-3-(3,4-dihydroxybenzyl)aminoepicatechin (compound DC-0079); 3-deoxy-3-(3,4-dihydroxyphenethyl)aminoepicatechin (compound DC-0080); 2,3,6,7-tetrahydroxy-9,10-epoxy-9,10-dihydroacridine (compound DC-0081); 10-aminoanthracene-1,2,7,8-tetraol (compound DC-0082); acridine-1,2,6,7-tetraol (compound DC-0083); phenoxazine-2,3,7,8,10-pentaol (compound DC-0084); dibenzo[c,f][2,7]napthyridine-2,3,10,11-tetraol (compound DC-0085); and 6-methyl-5,6,6a,7-tetrahydro-4H-dibenzo[de,g]quinoline-2,10,11-triol (compound DC-0086);

(3) the methylenedioxy analogs and pharmaceutically acceptable esters of compounds of (1) and (2); and
(4) the pharmaceutically acceptable salts of the compounds of (1) to (3).

Other compounds of the invention for use in the modulation of tau aggregation and dissolution/disruption/inhibition of tau aggregates are compounds of the formula:

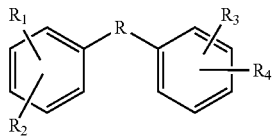

where:
$R_1$ and $R_2$, and $R_3$ and $R_4$ are hydroxyl groups independently positioned at one of the positions selected from the group consisting of 2,3; 2,4; 2,5; 2,6; 3,5; 3,6; 4,5; 4,6 and 5,6, and R is selected from a sulfonamide, heteroaryl, tricycloalkyl and —C(I)NR' where R' is selected from H or $CH_3$ or pharmaceutically acceptable esters or salts thereof and compounds;

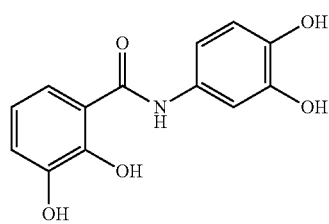 [SMILES: O=C(Nc1ccc(O)c(O)c1)c1cccc(O)c1O]

2,3 dihydroxybenzoic acid 3,4 dihydroxyanilide (DC-51-OH1),

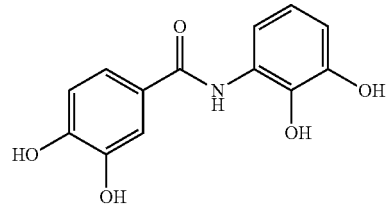 [SMILES: O=C(Nc1cccc(O)c1O)c1ccc(O)c(O)c1]

3,4 dihydroxybenzoic acid 2,3 dihydroxyanilide (DC-51-OH2),

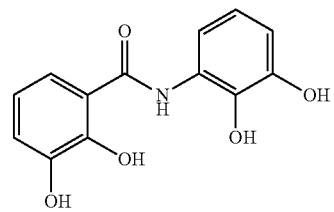 [SMILES: O=C(Nc1cccc(O)c1O)c1cccc(O)c1O]

2,3 dihydroxybenzoic acid 2,3 dihydroxyanilide (DC-51-OH3),

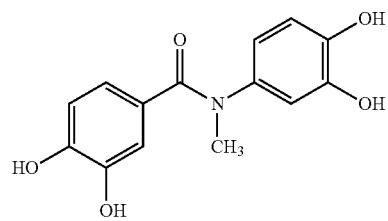 [SMILES: CN(C(=O)c1ccc(O)c(O)c1)c1ccc(O)c(O)c1]

3,4 dihydroxybenzoic acid 3,4 dihydroxy N-methyl anilide (DC-51-CH3),

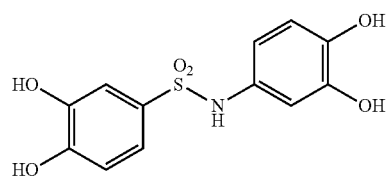 [SMILES: O=S(=O)(Nc1ccc(O)c(O)c1)c1ccc(O)c(O)c1]

3,4 dihydroxybenzenesulfonic acid 3,4 dihydroxyphenylsulfonamide (DC-51-W1),

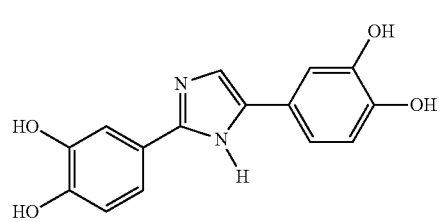 [SMILES: Oc1ccc(-c2cnc(-c3ccc(O)c(O)c3)[nH]2)cc1O]

2,4 bis(3,4 dihydroxyphenyl) imidazole (DC-51-W2),

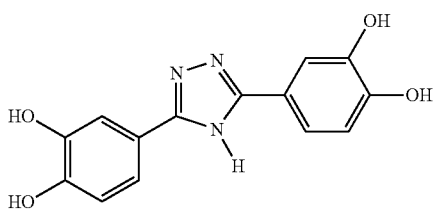 [SMILES: Oc1ccc(-c2nnc(-c3ccc(O)c(O)c3)[nH]2)cc1O]

3,5 bis(3,4 dihydroxyphenyl) 1,2,4 triazole (DC-51-W3),

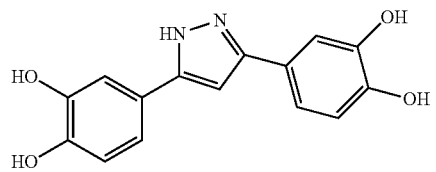 [SMILES: Oc1ccc(-c2cc(-c3ccc(O)c(O)c3)[nH]n2)cc1O]

3,5 bis(3,4 dihydroxyphenyl)pyrazole (DC-51-W4),

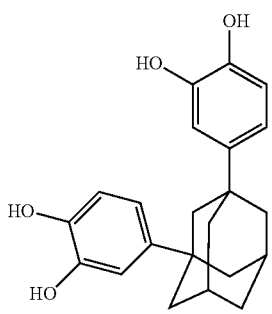 [SMILES: Oc1ccc(C23CC4CC(C2)CC(c2ccc(O)c(O)c2)(C4)C3)cc1O]

1,3 bis(3,4 dihydroxyphenyl) adamantane (DC-51-W5).

In a second aspect, this invention is a method of alleviating tauopathies in a mammal, especially a human, by administration of a therapeutically effective amount of a compound of the first aspect of this invention, for example as a pharmaceutical composition.

In a third aspect, this invention is the use of a compound of the first aspect of this invention in the manufacture of a medicament for allievating tauopathies.

DETAILED DESCRIPTION OF THE INVENTION

Definitions

In this application, the following terms shall have the following meanings, without regard to whether the terms are used varyingly elsewhere in the literature or otherwise in the known art.

Alleviating or alleviation is used considering the standard dictionary definition which is to make something such as pain or hardship more bearable or less severe. With respect to alleviating tauopathies, the person of skill in the art would understand that the compounds of this invention specifically act to reduce or diminish tau protein aggregates which are pathological hallmarks of the tauopathies. Therefore alleviating a tauopathy refers to removing or diminishing the occurrence of pathological hallmarks of the disease.

Chemical structures for each of the compounds of this invention (with the note that the acetates are shown as representative of the pharmaceutically acceptable esters as a class) are shown in this or the parent application. The names of the compounds are variously IUPAC names [names derived according to the accepted IUPAC (International Union of Pure and Applied Chemistry) system established by the coalition of the Commission on Nomenclature of Organic Chemistry and the Commission on Physical Organic Chemistry, as can be found at http://www.chem.mul.ac.uk/iupac], names derived from IUPAC names by addition or substitution (for example, by the use of "3,4-methylenedioxyphenyl" derived from "phenyl" instead of "benzo[1,3]dioxol-5-yl"), and names derived from the names of reactants (for example, by the use of "3,4-dihydroxybenzoic acid 3,4-dihydroxyanilide" instead of "N-(3, 4-dihydroxyphenyl)-3,4-dihydroxybenzamide"). The chemicals within the specification will be typically be referred to by DC-##. The compounds of the invention are referred to generally as bis- and tris-dihydroxyaryl compounds, or sometimes just as "dihydroxyaryl compounds". It will be noted that compound #84 has an additional hydroxy group, but does have two dihydroxyaryl groups; while compound #86 has only one dihydroxyaryl group but has an additional phenolic hydroxyl moiety.

"Methylenedioxy analogs" refers to the compounds of this invention in which each of the pairs of adjacent hydroxyl moieties of the dihydroxyaryl groups have been replaced by methylenedioxy groups. The methylenedioxy compounds are illustrated and referred to as compounds #1B to #86B or DC-0001B to DC-0086B. The methylenedioxy groups also are convenient intermediate protecting groups for the dihydroxy moieties and therefore these disclosed compounds are believed to also serve as effective prodrugs. The methylenedioxy analogs #1B to #80B are illustrated in Example 30 of the parent application.

"Pharmaceutically acceptable esters" refers to the compounds of this invention where the hydroxyl moieties of the dihydroxyaryl groups of the compounds are esterified with an acid or acids that result in a pharmaceutically acceptable poly(ester). The compounds are shown in Example 31 as acetylated, and these acetylated compounds are illustrated and referred to as compounds #1C to #86C or DC-0001C to DC-0086C; but it should be understood that the depiction of acetyl esters in Example 31 of the parent application, is merely illustrative, and all pharmaceutically acceptable esters are included within this invention. The ester groups are expected to serve as intermediate protecting groups for the hydroxyl moieties and therefore the pharmaceutically acceptable esters are expected to serve as effective prodrugs for their underlying bis- and tris-dihydroxyaryl compounds.

"Mammal" includes both humans and non-human mammals, such as companion animals (cats, dogs, and the like), laboratory animals (such as mice, rats, guinea pigs, and the like) and farm animals (cattle, horses, sheep, goats, swine, and the like).

"Pharmaceutically acceptable excipient" means an excipient that is conventionally useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

"Pharmaceutically acceptable salt" means a salt that is pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid-mono-salt or a di-salt; and similarly where there are more than two acidic groups present, some or all of such groups can be salified.

A "therapeutically effective amount" in general means the amount that, when administered to a subject or animal for alleviating a disease, and is sufficient to affect the desired degree of treatment for the disease or reduce or diminish pathological hallmarks associated with the disease. For example, reducing tau aggregates associated with Alzheimer's disease or another tauopathy. A "therapeutically effective amount" or a "therapeutically effective dosage" preferably modulates or inhibits, causes dissolution, and/or disrupts, abnormal tau aggregation, or contributes towards the treatment of a disease associated with these conditions, such as Alzheimer's disease (AD), Pick's disease (PiD), progressive supranuclear palsy (PSP), corticobasal degeneration (CBD) and familial frontotemporal dementia/Parkinsonism linked to chromosome 17 (FTDP-17), amyotrophic lateral sclerosis/Parkinsonism-dementia complex, argyrophilic grain dementia, dementia pugilistic, diffuse neurofibrillary tangles with calcification, progressive subcortical gliosis and tangle only dementia. Effective amounts of a compound of this invention or composition thereof for treatment of a mammalian subject are about 0.1 to about 1000 mg/Kg of body weight of the subject/day, such as from about 1 to about 100 mg/Kg/day, especially from about 10 to about 100 mg/Kg/day. A broad range of disclosed composition dosages are believed to be both safe and effective.

"Treating" or "treatment" of a disease in general means modulating tau aggregation or the dissolution, disruption, and/or inhibition of abnormal tau aggregates associated with a tauopathy.

"A pharmaceutical agent" or "pharmacological agent" or "pharmaceutical composition" refers to a compound or combination of compounds used for treatment, preferably in a pure or near pure form. In the specification, pharmaceutical or pharmacological agents include the compounds of this invention. The compounds are desirably purified to 80% homogeneity, and preferably to 90% homogeneity. Compounds and compositions purified to 99.9% homogeneity are believed to be advantageous. As a test or confirmation, a suitable homogeneous compound on HPLC would yield what those skilled in the art would identify as a single sharp-peak band.

Use of compounds of the invention include
(1) compounds of the formula:

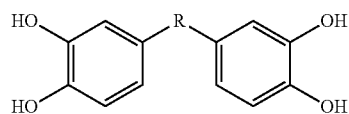

where:
R is a $C_1$-$C_{10}$ alkylene group, in which, when the number of carbon atoms is at least 2, there are optionally 1 or 2 non-adjacent double bonds; 1 to 3 non-adjacent methylene groups are optionally replaced by NR' (where R' is H, alkyl, or acyl), O, or S; and 1 or 2 methylene groups are optionally replaced by a carbonyl or hydroxymethylene group; and
(2) the compounds that are:
3,4,3',4'-tetrahydroxybenzoin (compound DC-001); 3,4,3',4'-tetrahydroxydesoxybenzoin (compound DC-002); 3,4,3',4'-tetrahydroxydiphenylmethane (compound DC-003); 1,2-bis(3,4-dihydroxyphenyl)ethane (compound DC-004); 1,3-bis(3,4-dihydroxyphenyl)propane (compound DC-005); 3,4,3',4'-tetrahydroxychalcone (compound DC-006); 3,5-bis(3,4-dihydroxyphenyl)-1-methyl-2-pyrazoline (compound DC-007); 4,6-bis(3,4-dihydroxyphenyl)-3-cyano-2-methylpyridine (compound DC-008); 1,4-bis(3,4-dihydroxybenzyl)piperazine (compound DC-009); N,N'-bis(3,4-dihydroxybenzyl)-N,N'-dimethylethylenediamine (compound DC-0010); 2,5-bis(3,4-dihydroxybenzyl)-2,5-diaza[2.2.1]bicycloheptane (compound DC-0011); N,N'-bis(3,4-dihydroxybenzyl)-trans-1,2-diaminocyclohexane (compound DC-0012); N,N'-bis(3,4-dihydroxybenzyl)-trans-1,4-diaminocyclohexane (compound DC-0013); N,N'-bis(3,4-dihydroxybenzyl)-cis-1,3-bis(aminomethyl)cyclohexane (compound DC-0014); N-(3,4-dihydroxybenzyl)proline 3,4-dihydroxybenzylamide (compound DC-0015); 2-(3,4-dihydroxybenzyl)isoquinoline-3-carboxylic acid 3,4-dihydroxyphenethylamide (compound DC-0016); 2,6-bis(3,4-dihydroxybenzyl)-cyclohexanone (compound DC-0017); 3,5-bis(3,4-dihydroxybenzyl)-1-methyl-4-piperidinone (compound DC-0018); 2,4-bis(3,4-dihydroxybenzyl)-3-tropinone (compound DC-0019); tris-(3,4-dihydroxybenzyl)methane (compound DC-0020); α-(3,4-dihydroxybenzamido)-3,4-dihydroxycinnamic acid 3,4-dihydroxybenzyl amide (compound DC-0021); 4-(3,4-dihydroxybenzylaminomethylene)-2-(3,4-dihydroxyphenyl)oxazolin-5-one (compound DC-0022); 1,4-bis(3,4-dihydroxybenzoyl)piperazine (compound DC-0023); N,N'-bis(3,4-dihydroxybenzoyl)-N,N'-dimethylethylenediamine (compound DC-0024); 2,5-bis(3,4-dihydroxybenzoyl)-2,5-diaza[2.2.1]bicycloheptane (compound DC-0025); N,N'-bis(3,4-dihydroxybenzoyl)-trans-1,2-diaminocyclohexane (compound DC-0026); N,N'-bis(3,4-dihydroxybenzoyl)-cis-1,3-bis(aminomethyl)cyclohexane (compound DC-0027); 3,6-bis(3,4-dihydroxybenzyl)-2,5-diketopiperazine (compound DC-0028); 3,6-bis(3,4-dihydroxybenzylidene)-1,4-dimethyl-2,5-diketopiperazine (compound DC-0029); N-(3,4-dihydroxyphenylacetyl)proline 3,4-dihydroxyanilide (compound DC-0030); 2,3-bis(3,4-dihydroxyphenyl)butane (compound DC-0031); 1,3-bis(3,4-dihydroxybenzyl)benzene (compound DC-0032); 1,4-bis(3,4-dihydroxybenzyl)benzene (compound DC-0033); 2,6-bis(3,4-dihydroxybenzyl)pyridine (compound DC-0034); 2,5-bis(3,4-dihydroxybenzyl)thiophene (compound DC-0035); 2,3-bis(3,4-dihydroxybenzyl)thiophene (compound DC-0036); 1,2-bis(3,4-dihydroxyphenyl)cyclohexane (compound DC-0037); 1,4-bis(3,4-dihydroxyphenyl)cyclohexane (compound DC-0038); 3,7-bis(3,4-dihydroxyphenyl)bicyclo[3.3.0]octane (compound DC-0039); 2,3-bis(3,4-dihydroxyphenyl)-1,7,7-trimethylbicyclo[2.2.1]heptane (compound DC-0040); 1,2-bis(3,4-dihydroxyphenoxy)ethane (compound DC-0041); 1,3-bis(3,4-dihydroxyphenoxy)propane (compound DC-0042); trans-1,2-bis(3,4-dihydroxyphenoxy)-cyclopentane (compound DC-0043); N-(3,4-dihydroxybenzyl)-3-(3,4-dihydroxyphenoxy)-2-hydroxypropylamine (compound DC-0044); 3,4-dihydroxyphenoxyacetic acid 3,4-dihydroxyanilide (compound DC-0045); 3,4-dihydroxyphenoxyacetic acid 3,4-dihydroxybenzylamide (compound DC-0046); 3,4-dihydroxyphenoxyacetic acid 3,4-dihydroxyphenethylamide (compound DC-0047); 3,4-dihydroxybenzoic acid p-(3,4-dihydroxyphenoxy)anilide (compound DC-0048); 3,4-dihydroxybenzoic acid o-(3,4-dihydroxyphenoxy)anilide (compound DC-0049); 2,6-bis(3,4-dihydroxyphenoxy)pyridine (compound DC-0050), 3,4-dihydroxybenzoic acid 3,4-dihydroxyanilide (compound DC-0051); 3,4-dihydroxybenzoic acid 3,4-dihydroxybenzylamide (compound DC-0052); 3,4-dihydroxybenzoic acid 3,4-dihydroxyphenethylamide (compound DC-0053); 3,4-dihydroxyphenylacetic acid 3,4-dihydroxyanilide (compound DC-0054); 3,4-dihydroxyphenylacetic acid 3,4-dihydroxybenzylamide (compound DC-0055); 3,4-dihydroxyphenylacetic acid 3,4-dihydroxyphenethylamide (compound DC-0056); 3-(3,4-dihydroxyphenyl)propionic acid 3,4-dihydroxyanilide (compound DC-0057); 3-(3,4-dihydroxyphenyl) propionic acid 3,4-dihydroxybenzylamide (compound DC-0058); 3-(3,4-dihydroxyphenyl)propionic acid 3,4-dihydroxyphenethylamide (compound DC-0059); 3,4-dihydroxycinnamic acid 3,4-dihydroxyanilide (compound DC-0060); 3,4-dihydroxycinnamic acid 3,4-dihydroxybenzylamide (compound DC-0061); 3,4-dihydroxycinnamic acid 3,4-dihydroxyphenethylamide (compound DC-0062); oxalic acid bis(3,4-dihydroxyanilide) (compound DC-0063); oxalic acid bis(3,4-dihydroxybenzylamide) (compound DC-0064); oxalic acid bis(3,4-dihydroxyphenethylamide) (compound DC-0065); succinic acid bis(3,4-dihydroxyanilide) (compound DC-0066); succinic acid bis(3,4-dihydroxybenzylamide) (compound DC-0067); succinic acid bis(3,4-dihydroxyphenethylamide) (compound DC-0068); maleic acid bis(3,4-dihydroxyanilide) (compound DC-0069); maleic acid bis (3,4-dihydroxybenzylamide) (compound DC-0070); fumaric acid bis(3,4-dihydroxyanilide) (compound DC-0071); fumaric acid bis(3,4-dihydroxybenzylamide) (compound DC-0072); bis(3,4-dihydroxybenzyl)amine (compound DC-0073); N-(3,4-dihydroxybenzyl)-3,4-dihydroxyphenethylamine (compound DC-0074); tris(3,4-dihydroxybenzyl)amine (compound DC-0075); 1,3-bis(3,4-dihydroxyphenyl)urea (compound DC-0076); 1-(3,4-dihydroxyphenyl)-3-(3,4-dihydroxybenzyl)urea (compound DC-0077); 1-(3,4-dihydroxyphenyl)-3-(3,4-dihydroxyphenethyl)urea (compound DC-0078); 3-deoxy-3-(3,4-dihydroxybenzyl)aminoepicatechin (compound DC-0079); 3-deoxy-3-(3,4-dihydroxyphenethyl)aminoepicatechin (compound DC-0080); 2,3,6,7-tetrahydroxy-9,10-epoxy-9,10-dihydroacridine (compound DC-0081); 10-aminoanthracene-1,2,7,8-tetraol (compound DC-0082); acridine-1,2,6,7-tetraol (compound DC-0083); phenoxazine-2,3,7,8,10-pentaol (compound DC-0084); dibenzo[c,f][2,7]napthyridine-2,3,10,11-tetraol (compound DC-0085); and 6-methyl-5,6,6a,7-tetrahydro-4H-dibenzo[de,g]quinoline-2,10,11-triol (compound DC-0086);

(3) the methylenedioxy analogs and pharmaceutically acceptable esters of compounds of (1) and (2); and (4) the pharmaceutically acceptable salts of the compounds of (1) to (3).

Other compounds of the invention for use are:
compounds of the formula:

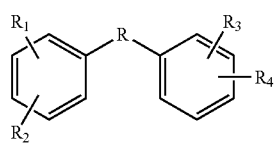

where:

$R_1$ and $R_2$, and $R_3$ and $R_4$ are hydroxyl groups independently positioned at one of the positions selected from the group consisting of 2,3; 2,4; 2,5; 2,6; 3,5; 3,6; 4,5; 4,6 and 5,6, and R is selected from a sulfonamide, heteroaryl, tricycloalkyl and —C(O)NR' where R' is selected from H or $CH_3$ or pharmaceutically acceptable esters or salts thereof.

The compounds of this invention for use are also:

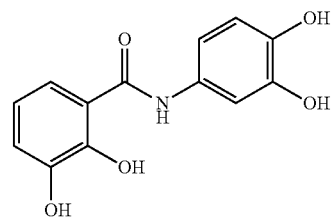 [SMILES: O=C(Nc1ccc(O)c(O)c1)c1cccc(O)c1O]

2,3 dihydroxybenzoic acid 3,4 dihydroxyanilide (DC-51-OH1),

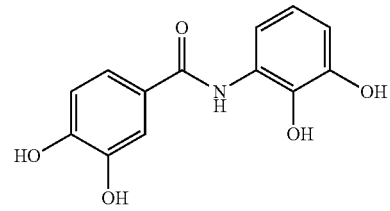 [SMILES: O=C(Nc1cccc(O)c1O)c1ccc(O)c(O)c1]

3,4 dihydroxybenzoic acid 2,3 dihydroxyanilide (DC-51-OH2),

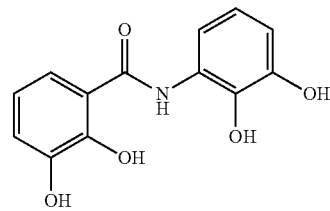 [SMILES: O=C(Nc1cccc(O)c1O)c1cccc(O)c1O]

2,3 dihydroxybenzoic acid 2,3 dihydroxyanilide (DC-51-OH3),

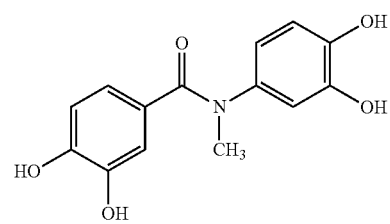 [SMILES: CN(C(=O)c1ccc(O)c(O)c1)c1ccc(O)c(O)c1]

3,4 dihydroxybenzoic acid 3,4 dihydroxy N-methyl anilide (DC-51-CH3),

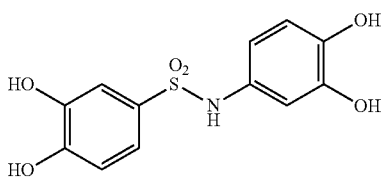 [SMILES: O=S(=O)(Nc1ccc(O)c(O)c1)c1ccc(O)c(O)c1]

3,4 dihydroxybenzenesulfonic acid 3,4 dihydroxyphenylsulfonamide (DC-51-W1),

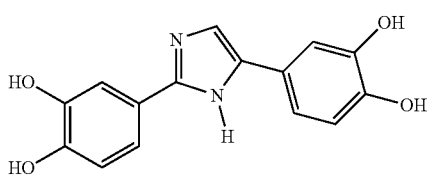 [SMILES: Oc1ccc(-c2cnc(-c3ccc(O)c(O)c3)[nH]2)cc1O]

2,4 bis (3,4 dihydroxyphenyl) imidazole (DC-51-W2),

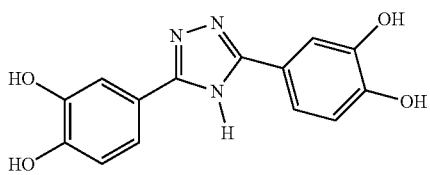 [SMILES: Oc1ccc(-c2nnc(-c3ccc(O)c(O)c3)[nH]2)cc1O]

3,5 bis(3,4 dihydroxyphenyl) 1,2,4 triazole (DC-51-W3),

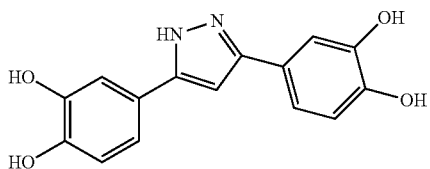 [SMILES: Oc1ccc(-c2cc(-c3ccc(O)c(O)c3)[nH]n2)cc1O]

3,5 bis(3,4 dihydroxyphenyl)pyrazole (DC-51-W4),

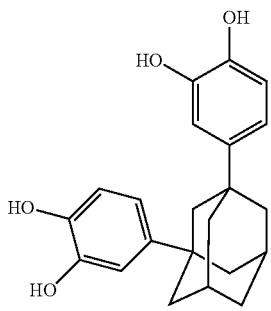 [SMILES: Oc1ccc(C23CC4CC(C2)CC(c2ccc(O)c(O)c2)(C4)C3)cc1O]

1,3 bis(3,4 dihydroxyphenyl) adamantane (DC-51-W5),

Synthesis of the Compounds of the Invention

The compounds of this invention may be prepared by methods generally known to the person of ordinary skill in the art, having regard to that knowledge and the disclosure of this application and its priority applications, the contents of which are incorporated by reference.

The starting materials and reagents used in preparing these compounds are either available from commercial suppliers such as the Aldrich Chemical Company (Milwaukee, Wis.), Bachem (Torrance, Calif.), Sigma (St. Louis, Mo.), or Lancaster Synthesis Inc. (Windham, N.H.) or are prepared by methods well known to a person of ordinary skill in the art, following procedures described in such references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

Other starting materials or early intermediates may be prepared by elaboration of the materials listed above, for example, by methods well known to a person of ordinary skill in the art.

The starting materials, intermediates, and compounds of this invention may be isolated and purified using conventional techniques, including precipitation, filtration, distillation, crystallization, chromatography, and the like. The compounds may be characterized using conventional methods, including physical constants and spectroscopic methods.

Pharmacology and Utility

The use of the compounds of this invention, either as the dihydroxyaryl compounds per se, or as the methylenedioxy analogs or pharmaceutically acceptable esters (once de-protected either in the body or in vitro), or the compounds set out herein to modulate tau aggregation or to cause the dissolution, disruption and/or inhibition of tau aggregates and for alleviating tauopathies. Their activity can be measured in vitro by methods such as those discussed in Example 1, while their activity in vivo against tauopathies can be measured in animal models, such as those transgenic mouse models that mimic AD and other tauopathies, and in humans (Dickey, C et al., 2009 μm J Pathol. 174(1):228-38; Boimel, M et al., 2009 J Neuropathol Exp Neurol 68(3): 314-25; and Lopes, J P et al., 2009 J Alzh Dis 16(3):541-9.)

"Tauopathies" suitable for alleviation with the compounds of this invention are diseases associated with abnormal tau aggregation are Alzheimer's disease (AD), Pick's disease (PiD), progressive supranuclear palsy (PSP), corticobasal degeneration (CBD) and familial frontotemporal dementia/Parkinsonism linked to chromosome 17 (FTDP-17), amyotrophic lateral sclerosis/Parkinsonism-dementia complex, argyrophilic grain dementia, dementia pugilistic, diffuse neurofibrillary tangles with calcification, progressive subcortical gliosis and tangle only dementia.

Pharmaceutical Compositions and Administration

In general, compounds of the invention will be administered in therapeutically effective amounts by any of the usual modes known in the art, either singly or in combination with at least one other compound of this invention and/or at least one other conventional therapeutic agent for the disease being treated. A therapeutically effective amount may vary widely depending on the disease, its severity, the age and relative health of the animal being treated, the potency of the compound(s), and other factors. As tau protein modulators or aggregation inhibitors, therapeutically effective amounts of compounds of this invention may range from 0.1-1000 mg/Kg body weight/day, such as from 1-100 mg/Kg/day; for example, 10-100 mg/Kg/day. A person of ordinary skill in the art will be conventionally able, and without undue experimentation, having regard to that skill and to this disclosure, to determine a therapeutically effective amount of a compound for the alleviation of tau aggregation or tauopathy.

Preferred compositions will contain a compound of this invention that is at least substantially pure. In general "pure" means better than 95% pure, and "substantially pure" means a compound synthesized such that the compound, as made as available for consideration into a therapeutic dosage, has only those impurities that can not readily nor reasonably be removed by conventional purification processes.

In general, the compounds of this invention will be administered as pharmaceutical compositions by one of the following routes: oral, topical, systemic (e.g. transdermal, intranasal, or by suppository), or parenteral (e.g. intramuscular, subcutaneous, or intravenous injection). Compositions may take the form of tablets, pills, capsules, semisolids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as Remington: The Science and Practice of Pharmacy, A. Gennaro, ed., 20th edition, Lippincott, Williams & Wilkins, Philadelphia, Pa. Suitable liquid carriers, especially for injectable solutions, include water, aqueous saline solution, aqueous dextrose solution, and glycols.

In particular, the compound(s)—optimally only one such compound is administered in any particular dosage form—can be administered, orally, for example, as tablets, troches, lozenges, aqueous or oily suspension, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Tablets contain the compound in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, maize starch or alginic acid; binding agents, for example, maize starch, gelatin or acacia, and lubricating agents, for example, magnesium stearate or stearic acid or talc. The tablets may be uncoated or they may be coated by known techniques to delay disintegration and absorption in the gastrointestinal tract and thereby provide a sustained action over a longer period. For example, a time delay material such as glycerol monostearate or glycerol distearate may be employed. Formulations for oral use may also be presented as hard gelatin capsules wherein the compound is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Aqueous suspensions contain the compound in admixture with excipients suitable for the manufacture of aqueous suspensions. Such excipients are suspending agents, for example, sodium carboxymethylcellulose, methylcellulose, hydroxypropylmethyl cellulose, sodium alginate, polyvinylpyrrolidone, gum tragacanth and gum acacia; dispersing or wetting agents may be naturally occurring phosphatides, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids such as hexitol such as polyoxyethylene sorbitol monooleate, or condensation products of ethylene oxide with partial esters from fatty acids and a hexitol anhydrides, for example, polyethylene sorbitan monooleate. The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the compound in a vegetable oil, for example arachis oil, olive oil, sesame oil, or coconut oil or in a mineral oil such as liquid paraffin. The oily suspensions may contain a thickening agent, for example beeswax, hard paraffin or cetyl alcohol. Sweetening agents, such as those set forth below, and flavoring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already described above. Additional excipients, for example sweetening, flavoring and agents, may also be present.

The compounds of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean, lecithin, and occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsion may also contain sweetening and flavoring agents. Syrups and elixirs may be formulated with sweetening agents, for example, glycerol, sorbitol or sucrose. Such formulations may also contain a demulcent, a preservative and flavoring and coloring agents.

The compounds of the invention can also be administered by injection or infusion, either subcutaneously or intravenously, or intramuscularly, or intrasternally, or intranasally, or by infusion techniques in the form of sterile injectable or oleaginous suspension. The compound may be in the form of a sterile injectable aqueous or oleaginous suspensions. These suspensions may be formulated according to the known art using suitable dispersing of wetting agents and suspending agents that have been described above. The sterile injectable preparation may also be a sterile injectable solution or suspension in a non-toxic parenterally-acceptable diluent or solvent for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oils may be conventionally employed including synthetic mono- or diglycerides. In addition fatty acids such as oleic acid find use in the preparation of injectables. Dosage regimens can be adjusted to provide the optimum therapeutic response. For example, several divided dosages may be administered daily or the dosage may be proportionally reduced as indicated by the exigencies of the therapeutic situation.

It is especially advantageous to formulate the compounds in dosage unit form for ease of administration and uniformity of dosage. Dosage unit form as used herein refers to physically discrete units suited as unitary dosages for the subjects to be treated; each containing a therapeutically effective quantity of the compound and at least one pharmaceutical excipient. A drug product will comprise a dosage unit form within a container that is labeled or accompanied by a label indicating the intended method of treatment, such as the treatment of a tauopathy or disease associated with abnormal tau aggregation.

Sustained Release Formulations

The invention also includes the use of sustained release formulations to deliver the compounds of the present invention to the desired target (i.e. brain or systemic organs) at high circulating levels (between $10^{-9}$ and $10^{-4}$ M) are also disclosed. In a preferred embodiment for the treatment of Alzheimer's or other tauopathies, the circulating levels of the compounds is maintained up to $10^{-7}$ M. The levels are either circulating in the patient systemically, or in a preferred embodiment, present in brain tissue, and in a most preferred embodiment, localized to the areas of abnormal tau aggregation.

It is understood that the compound levels are maintained over a certain period of time as is desired and can be easily determined by one skilled in the art using this disclosure and compounds of the invention. In a preferred embodiment, the invention includes a unique feature of administration comprising a sustained release formulation so that a constant level of therapeutic compound is maintained between $10^{-8}$ and $10^{-6}$M between 48 to 96 hours in the sera.

Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein, may be readily selected for use with the pharmaceutical compositions of the invention. Thus, single unit dosage forms suitable for oral administration, such as, but not limited to, tablets, capsules, gelcaps, caplets, powders and the like, that are adapted for sustained release are encompassed by the present invention.

In a preferred embodiment, the sustained release formulation contains active compound such as, but not limited to, microcrystalline cellulose, maltodextrin, ethylcellulose, and magnesium stearate. As described above, all known methods for encapsulation which are compatible with properties of the disclosed compounds are encompassed by this invention. The sustained release formulation is encapsulated by coating particles or granules of the pharmaceutical composition of the invention with varying thickness of slowly soluble polymers or by microencapsulation. In a preferred embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one preferred embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, having a relatively high percentage of plasticizer in the coating in order to permit sufficient flexibility to prevent substantial breakage during compression are disclosed. The specific amount of plasticizer varies depending on the nature of the coating and the particular plasticizer used. The amount may be readily determined empirically by testing the release characteristics of the tablets formed. If the medicament is released too quickly, then more plasticizer is used. Release characteristics are also a function of the thickness of the coating. When substantial amounts of plasticizer are used, the sustained release capacity of the coating diminishes. Thus, the thickness of the coating may be increased slightly to make up for an increase in the amount of plasticizer. Generally, the plasticizer in such an embodiment will be present in an amount of about 15 to 30% of the sustained release material in the coating, preferably 20 to 25%, and the amount of coating will be from 10 to 25% of the weight of the active material, preferably 15 to 20%. Any conventional pharmaceutically acceptable plasticizer may be incorporated into the coating.

The compounds of the invention can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations of the invention are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds. The term "sustained release component" in the context of the present invention is defined herein as a compound or compounds, including, but not limited to, polymers, polymer matrices, gels, permeable membranes, liposomes, microspheres, or the like, or a combination thereof, that facilitates the sustained release of the active ingredient.

If the complex is water-soluble, it may be formulated in an appropriate buffer, for example, phosphate buffered saline, or other physiologically compatible solutions. Alternatively, if the resulting complex has poor solubility in aqueous solvents, then it may be formulated with a non-ionic surfactant such as Tween, or polyethylene glycol. Thus, the compounds and their physiologically solvents may be formulated for administration by inhalation or insufflation (either through the mouth or the nose) or oral, buccal, parenteral, or rectal administration, as examples.

Preparations for oral administration may be suitably formulated to give controlled release of the active compound. In a preferred embodiment, the compounds of the present invention are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compounds of the invention may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachis, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and nontoxic, include but are not limited to hydrogels, silicones, polyethylenes, ethylene-vinyl acetate copolymers, or biodegradable polymers.

The following non-limiting Examples are given by way of illustration only and are not considered a limitation of this invention, many apparent variations of which are possible without departing from the spirit or scope thereof.

EXAMPLES

Example 1

Compounds of this Invention are Potent Disrupters of Tau Aggregates

The compounds set out above were found to be potent in the dissolution/disruption/inhibition of Tau tangles or Tau aggregates. In a set of studies, the efficacy of the compounds to cause a dissolution/disassembly/disruption of pre-formed Tau aggregates was analyzed.

Part A—Thioflavin T Fluorometry Data

Thioflavin T fluorometry was used in this study to determine the effects of the compounds compared to a negative control peptide. Thioflavin T binds specifically to aggregated Tau or Tau tangles, and this binding produces a fluorescence enhancement at 485 nm that is directly proportional to the amount of aggregated Tau. The higher the fluorescence, the greater the amount of aggregated Tau.

In this study, Tau-441 was pre-fibrillized or aggregated by combining with Heparin (SIGMA) at 1:1 wt/wt, then incubation at 37° C. and shaking at 1400 rpm for 8 days. Following the pre-fibrillization, 30 µg of aggregated Tau-441 (rPeptide) was then incubated at 37° C. for 3 days either alone, or in the presence of one of the compounds or negative control (at Tau:test compound weight ratios of 1:1, 1:0.1, 1:0.01 or 1:0.001). Following 3-days of co-incubation, 50 µl of each incubation mixture was transferred into a 96-well microtiter plate containing 150 µl of distilled water and 50 µl of a Thioflavin T solution (i.e. 500 mM Thioflavin T in 250 mM phosphate buffer, pH 6.8). The fluorescence was read at 485 nm (444 nm excitation wavelength) using an ELISA plate fluorometer after subtraction with buffer alone or compound alone, as blank.

The results are presented in the table below. For example, as expected, the negative control caused no significant dissolution/disruption/inhibition of preformed Tau aggregates at all of the concentrations tested, in contrast, the compounds all caused a dose-dependent dissolution/disruption/inhibition of preformed Tau aggregates. All the compounds tested, with the exception of DC-0023 and DC-0063, were highly efficacious in their ability to disrupt preformed Tau aggregates. For example, DC-51-W2 caused a significant ($p<0.01$) 92.4±1.23% dissolution/disruption/inhibition when used at a Tau:test compound wt/wt ratio of 1:0.1, and a 74.0±4.01% dissolution/disruption/inhibition when used at a Tau:compound wt/wt ratio of 1:0.01. Under the same conditions (i.e. Tau:test compound wt/wt ratio of 1:0.1), compound DC-004 caused a 92.8±2.59% dissolution/disruption/inhibition, and a 68.0±1.71% dissolution/disruption/inhibition when used at a Tau:compound wt/wt ratio of 1:0.01. This study indicated that the compounds of this invention can result in the potent dissolution, disruption and/or inhibition of Tau aggregates, and typically exert their effects in a dose-dependent manner.

TABLE 1

Thioflavin T fluorometry data - dissolution/disruption/inhibition of Tau aggregates
% dissolution/disruption/inhibition Tau (result ± S.D.)
at Tau:test compound wt/wt ratio

| Test Compound # | 1:1 | 1:0.1 | 1:0.01 | 1:0.001 |
|---|---|---|---|---|
| Negative control | 15.4 ± 3.97 | 11.5 ± 2.85 | 11.2 ± 3.47 | 11.1 ± 1.98 |
| DC-003 | 91.2 ± 2.59 | 89.2 ± 1.96 | 54.1 ± 2.62 | 17.0 ± 2.49 |
| DC-004 | 93.5 ± 4.42 | 92.8 ± 2.59 | 68.0 ± 1.71 | 19.3 ± 0.00 |
| DC-0021 | 94.8 ± 2.59 | 75.2 ± 2.04 | 31.7 ± 5.45 | 9.8 ± 2.95 |
| DC-0023 | 71.3 ± 2.04 | 33.4 ± 1.49 | 15.2 ± 2.49 | 11.4 ± 1.14 |
| DC-0051 | 96.1 ± 0.56 | 87.9 ± 5.03 | 51.5 ± 5.51 | 11.8 ± 4.67 |
| DC-0051-C | 92.2 ± 2.04 | 81.7 ± 4.07 | 38.6 ± 6.59 | 5.2 ± 6.04 |
| DC-0063 | 77.8 ± 1.13 | 34.7 ± 1.69 | 16.5 ± 2.49 | 11.8 ± 8.06 |
| DC-0076 | 94.1 ± 2.99 | 91.2 ± 0.56 | 54.1 ± 2.62 | 17.4 ± 4.88 |
| DC-51-OH1 | 100.0 ± 1.62 | 90.0 ± 2.14 | 58.0 ± 2.05 | 13.2 ± 5.38 |
| DC-51-OH2 | 100.0 ± 3.38 | 88.1 ± 2.85 | 43.7 ± 3.38 | 10.6 ± 5.36 |
| DC-51-OH3 | 100.0 ± 2.94 | 86.0 ± 5.69 | 61.5 ± 2.05 | 12.4 ± 5.38 |
| DC-51-CH3 | 100.0 ± 0.89 | 90.0 ± 2.43 | 59.4 ± 2.61 | 13.0 ± 5.06 |
| DC-51-W1 | 100.0 ± 1.55 | 87.3 ± 1.69 | 50.2 ± 4.96 | 16.5 ± 2.48 |
| DC-51-W2 | 97.7 ± 1.95 | 92.4 ± 1.23 | 74.0 ± 4.01 | 25.7 ± 4.90 |
| DC-51-W3 | 100.0 ± 1.62 | 90.3 ± 2.04 | 37.2 ± 4.96 | 6.0 ± 5.12 |
| DC-51-W4 | 100.0 ± 4.32 | 88.9 ± 6.74 | 57.7 ± 24.96 | 11.9 ± 3.28 |
| DC-51-W5 | 96.6 ± 2.80 | 91.1 ± 0.81 | 35.2 ± 2.59 | 7.6 ± 3.38 |

Example 2

Cloning of Tau Repeat Domains (TauRD) into a Tetracycline-Inducible Mammalian Expression Vector Total RNA was isolated from human adult non-demented frontal tissues obtained at autopsy from the University of Washington ADRC Brain Bank and immediately frozen at 80° C. Single stranded cDNA was synthesized using M-MLV Reverse Transcriptase (Invitrogen; Carlsbad, Calif., USA) and random priming with hexameric primers (Invitrogen). All other primers used were also synthesized by Invitrogen. Tetracycline-inducible mammalian expression constructs, pcDNA4/TO-TauRD, were generated by insertion of cDNA fragments encoding the human tau repeat domain (TauRD; amino acid residues 244-372 in REFSEQ mRNA ENST00000351559) into pcDNA™4/TO vector (Invitrogen). The vector allows tetracycline-regulated expression of the gene of interest in mammalian host cells when a pcDNA™6/TR construct (Invitrogen) is also co-expressed.

The wild type TauRD (TauRDWT) cDNA insert was amplified from human brain single stranded cDNA by PCR with a forward primer (Tau6+730F), overlapped with the cDNA sequences of residues 244-249, and a reverse primer (Tau1116+3R) overlapped with residues 364-372 of human tau (REFSEQ mRNA ENST00000351559). The PCR products were first cloned into a pDrive-UA cloning vector (QIAGEN; Valencia, Calif., USA) as instructed by the manufacturer to generate pDrive-TauRDWT. Mutant constructs that contain mutations of ΔK280, P301S, and P301L found in frontotemporal dementia with Parkinsonism-17 were made on the pDrive-TauRDWT backbone using a QuikChange® Site-Directed Mutagenesis Kit (Stratagene, La Jolla, Calif.), as instructed by the manufacturer. The mutations have been shown to increase Tau aggregations in vitro or in vivo (Brunden et al., 2009). After confirmed by DNA sequencing, the cDNA inserts in pDrive-TauRDWT, pDrive-TauRDΔK280, pDrive-TauRDP301S and pDrive-TauRDP301L were then released by EcoRI digestion of the plasmids, gel-purified with a gel extraction kit (QIAGEN) as instructed, and subcloned into a pcDNA™4/TO vector at EcoRI sites to generate pcDNA4/TO-TauRDWT, pcDNA4/TO-TauRDΔK280, pcDNA4/TO-TauRDP301S, and pcDNA4/TO-TauRDP301L expression constructs. The pcDNA4/TO-TauRD constructs are driven by a hybrid promoter consisting of the human cytomegalovirus immediate-early promoter and tetracycline operator 2 sites for high-level tetracycline-regulated expression in mammalian cells. In the absence of tetracycline, expression of the inserted TauRD is repressed by the binding of Tet repressor homodimers (expressed from pcDNA™6/TR) to the tetracycline operator 2 sites. Addition of tetracycline to the cells de-represses the hybrid promoter in pcDNA™4/TO, and allows expression of TauRD. Because expression of TauRD can form aggregates in the cells, long-term expression of aggregated TauRD may be toxic to cells (Khlistunova et al., 2006 JBC 281(2):1205-14). Use of the tetracycline-regulated constructs allows us to generate stable cell lines in which expression of TauRD is under the control by addition of tetracycline into cell culture media.

Example 3

Generation of Stable Transfected Inducible TauRD Cell Lines

Tetracycline-inducible cell lines stably transfected with pcDNA4/TO-TauRDWT, pcDNA4/TO-TauRDΔK280, pcDNA4/TO-TauRDP301S, and pcDNA4/TO-TauRDP301L were generated to assess TauRD aggregation in cell culture. TREx™-293 cells (Invitrogen; R710-07), modified human embryonic kidney 293 cells (ATCC; CRL-1573) by stable transfection of pcDNA™6/TR, were employed to generate the TauRD stable cell lines. Both parental cells (TREx™-293 cells) and their derivatives (TREx293-TauRD) (see below) were maintained in culture media supplemented with 5 μg/ml blasticidin for selection of pcDNA6/TR-containing cells. Cells were routinely cultured in a regular growth media (RGM) that contained Dulbecco's Modified Eagle Medium (DMEM) (Invitrogen) supplemented with 10% fetal bovine serum, penicillin (60 units/mL), streptomycin (60 μg/mL) and blasticidin (5 μg/ml) at 37° C. in a cell culture incubator supplemented with 5% $CO_2$.

To generate stable cell lines, TREx™-293 cells were grown to 70-80% confluence in 12-well plates, and transfected with 1.2 g of pcDNA4/TO-TauRDWT, pcDNA4/TO-TauRDAK280, pcDNA4/TO-TauRDP301S, or pcDNA4/TO-TauRDP301L. Transfection was mediated by polyethylenimines (Polysciences, Inc.) as described by Hu et al. (2005 JBC 280(13):12548-58). Twenty-four hours after transfection, cells were plated at low density (400-2000 cells/100 mm dish), and grown in RGM containing 0.4 mg/ml of Zeocin (Invitrogen) to select pcDNA4/TO-TauRD-containing stable colonies. After two weeks, stable colonies were picked, and sub-cultured. Stable expression of TauRD was confirmed by Western analysis of cell lysates with a rabbit anti-human Tau polyclonal antibody (DakoCytomation, Denmark), a mouse anti-Tau monoclonal antibody (DC4R; rPeptide, Bogart, Ga.), and/or a rabbit anti-pTau (Ser 262) (Santa Cruz Biotechnology, Inc., Santa Cruz, Calif.). The stable cell lines were maintained with Zeocin-containing RGM. TREx™-293 cells stably transfected with various pcDNA4/TO-TauRD constructs are referred as TREx293-TauRDWT, TREx293-TauRDxK280, TREx293-TauRDP301S, and TREx293-TauRDP301L cells.

Example 4

Western Analysis of Soluble/Insoluble TauRD Monomers and Oligomers in Cell Lysates Soluble/insoluble TauRD monomers and oligomers in lysates were prepared and analyzed as follows. TREx293-TauRDWT (clone B1) cells were grown in RGM supplemented with 0.4 mg/ml of Zeocin, 1 g/ml of tetracycline (Tet+), and with or without addition of compounds for 2 days. Cells were gently washed once with PBS, and were lysed in a cold lysis buffer 50 mM Tris-HCl, pH 7.5, 100 mM NaCl, and 0.5% Triton X-100, supplemented with Complete™ protease inhibitor cocktail tablets (Roche) at one tablet/25 ml lysis buffer on ice for 20 min. Cell lysates were collected with cell scrapers into centrifuge tubes, and centrifuged at 15,000×g at 4° C. for 15 min. The supernatants were collected as soluble fractions. Pellets were then dissolved in non-reduced 1× Laemmli buffer [2% sodium dodecyl sulfate (SDS), 10% glycerol, 0.002% bromphenol blue, 62.5 mM Tris HCl, pH 6.8] by shaking at 24° C. for 50 min, boiling for 5 min, and centrifuging at 15,000×g at 4° C. for 15 min. The supernatants were collected as insoluble fractions and were directly loaded on Western gels; the soluble fractions were diluted at 3:1 in 4× non-reduced Laemmli buffer before loading on Western gels.

Soluble/insoluble fractions of cell lysates were separated in 4-12% Bis/Tris Criterion XT gels (Bio-Rad) at 180 volts, with buffer systems recommended by the manufacturer. After electrophoresis, protein bands were transferred onto Immobilon-PSQ membranes in a tris/glycine transfer buffer (Bio-Rad) using Bio-Rad Criterion™ Blotters. The transfer was conducted at 0.25 A (constant) for 60 min at 4° C. All transferred membranes were blocked with 5% milk in PBS+ 0.05% Tween-20 for 30-60 min at room temperature, and incubated with a rabbit anti-human Tau polyclonal antibody (DakoCytomation, Denmark) at 1:10000 for overnight at 4° C., and then with HRP-conjugated secondary antibody (Vector) at 1:4000 at room temperature for 2 hrs. Protein bands were visualized with an ECL system (GE Healthcare) by exposing to autoradiography films. For re-probing membranes with different antibodies, membranes were stripped with a Restore™ Western blot stripping buffer (Thermo Scientific; Rockford, Ill.), and re-probed with mouse anti-α-tubulin (1:30,000) (Sigma; Saint Louis, Mo.), and/or anti-β-actin (1:200,000) (Chemicon International) monoclonal antibodies. Quantitation of relative intensities of protein bands on autoradiographic films was performed by image quantification with the ScionImage software (http://www.s-cioncorp.com) as instructed in the product manual.

Example 5

Treatment of Cultured Cells with Compound DC-51 and its Analogs

Stock solutions (100 mM) of the compounds were prepared in dimethyl sulfoxide (DMSO), aliquoted and stored at −80° C. before use. On the day before treatment, TREx293-TauRDWT (clone B1) cells were plated in 12-well culture plates with RGM, supplemented with 0.4 mg/ml of Zeocin. The plating density was optimized to reach 25-30% of confluence on next day. On the next day, cell culture media was replaced with 1 ml per well of RGM (eliminating blasticidin) supplemented with 1 g/ml of tetracycline (Tet+), and freshly-diluted test compounds at the final concentrations between 0.25-100 µM. Cells were then incubated at 37° C. in a cell culture incubator for total 48 hrs, with fresh tetracycline/compound-containing media changed every 24 hrs. After incubation, cell lysates were collected for Western analysis of aggregated TauRD as described.

Example 6

Effects of Compound DC-51 and its Analogs on Aggregation and Solubility of TauRD in Cultured Cells as Assessed by Western Analysis FIG. 1 of the priority application (U.S. Pat. No. 8,455,867) shows that compound DC-51 and its analogs modulate levels of TauRD oligomers and monomers in insoluble fractions of TREx293-TauRDWT (clone B1) cell cultures as assessed by Western analysis. TREx293-TauRDWT cells were treated with DMSO vehicle control (Lanes 2, 15 and 28 of FIG. 1 of the priority application (U.S. Pat. No. 8,455,867)), compound DC-51 (0.5 µM in lanes 9&12; 1 µM in lanes 10&13; 10 µM in lanes 11&14) and its analogs DC-51-W3 (10 µM in lanes 16&19; 40 µM in lanes 17&20; 80 µM in lanes 18&21), and DC-51-W4 (10 µM in lanes 22&25; 40 µM in lanes 23&26; 80 µM in lanes 24&27) in 12-well plates for 48 hrs (compound-containing fresh media were changed every 24 hrs). Each condition was in duplicate. After incubation, insoluble fractions of cell lysates were collected as described, and analyzed by Western analysis with a rabbit anti-human Tau antibody (FIG. 1A of the priority application (U.S. Pat. No. 8,455,867)), and then re-probed for α-tubulin as a soluble protein marker and a protein loading control (FIG. 1B of the priority application (U.S. Pat. No. 8,455,867)). Lysates of cells grown in the absence of tetracycline (Lanes 1; no TauRD expression) were also analyzed in parallel to show background bands derived from endogenous Tau.

FIG. 2 of the priority application (U.S. Pat. No. 8,455,867) shows that compound DC-51 and its analogs modulate levels of TauRD oligomers and monomers in soluble fractions of TREx293-TauRDWT (clone B1) cell cultures as assessed by Western analysis. TREx293-TauRDWT cells were treated with DMSO vehicle control (Lanes 2, 15 and 28), compound DC-51 (0.5 µM in lanes 9&12; 1 µM in lanes 10&13; µM in lanes 11&14) and its analogs DC-51-W3 (10

µM in lanes 16&19; 40 µM in lanes 17&20; 80 µM in lanes 18&21), and DC-51-W4 (10 µM in lanes 22&25; 40 µM in lanes 23&26; 80 µM in lanes 24&27) in 12-well plates for 48 hrs (compound-containing fresh media were every 24 hrs). Each condition was in duplicate. After incubation, soluble fractions of cell lysates were collected as described, and analyzed by Western analysis with a rabbit anti-human Tau antibody (FIG. 2A of the priority application (U.S. Pat. No. 8,455,867)), and then re-probed for α-tubulin as a soluble protein marker and a protein loading control (FIG. 2B of the priority application (U.S. Pat. No. 8,455,867)). Lysates of cells grown in the absence of tetracycline (Lane 1; no TauRD expression) were also analyzed in parallel to show background bands derived from endogenous Tau.

FIGS. 3a and 3b of the priority application (U.S. Pat. No. 8,455,867) show relative levels of soluble/insoluble TauRD oligomers and monomers in compound DC-51-treated TREx293-TauRDWT cell lysates by quantitative densitometric analysis of the Western blots shown in FIGS. 1&2 of the priority application (U.S. Pat. No. 8,455,867).

FIGS. 4a and 4b of the priority application (U.S. Pat. No. 8,455,867) show relative levels of soluble/insoluble TauRD oligomers and monomers in compound DC-51-W3-treated TREx293-TauRDWT cell lysates by quantitative densitometric analysis of the Western blots shown in FIGS. 1&2 of the priority application (U.S. Pat. No. 8,455,867).

FIGS. 5a and 5b of the priority application (U.S. Pat. No. 8,455,867) show relative levels of soluble/insoluble TauRD oligomers and monomers in compound DC-51-W4-treated TREx293-TauRDWT cell lysates by quantitative densitometric analysis of the Western blots shown in FIGS. 1&2 of the priority application (U.S. Pat. No. 8,455,867).

Example 7

Quantitative Analysis of Western Blots

A 50-55% reduction in levels of insoluble TauRD oligomers (30-300 kDa) (FIGS. 1A & 3A of the priority application (U.S. Pat. No. 8,455,867)), and a 67-83% reduction in levels of insoluble TauRD monomers (15 kDa) (FIGS. 1A & 3B of the priority application (U.S. Pat. No. 8,455,867)) was found in cells treated with 0.5-10 µM of compound DC-51, when compared to DMSO control (C) ($p<0.05$-$0.01$). Treatment with compound DC-51 exhibits no significant effects on levels of soluble TauRD oligomers, and monomers (FIGS. 2A & 3C-D of the priority application (U.S. Pat. No. 8,455,867)). The results indicate that compound DC-51 is a potential agent that can lower insoluble (aggregated) Tau when used at the lower range of micromolar levels.

A trend of reduction in levels of insoluble TauRD oligomers (30-300 kDa) was found in cells treated with 10-40 µM of compound DC-51-W3, when compared to DMSO control (C) ($p>0.05$) (FIGS. 1A & 4A of the priority application (U.S. Pat. No. 8,455,867)). A reduction in levels of insoluble TauRD monomers (15 kDa) was found in cells treated with 10 µM of the compound ($p<0.05$) (FIGS. 1A & 4B of the priority application (U.S. Pat. No. 8,455,867)). In addition, a 1.54-fold increase in levels of soluble TauRD oligomers, and a 45% reduction in levels of soluble TauRD monomers were found in cells treated with 10 µM, and 80 µM of the compound, respectively, when compared to the control ($p<0.05$)(FIGS. 2A & 4C-D). The results suggest that compound DC-51-W3 has effects on Tau aggregation under the experimental conditions.

A trend of increase in levels of insoluble TauRD oligomers (30-300 kDa), and a 65-76% reduction of insoluble TauRD monomers (15 kDa) ($p<0.05$) was also found in cells treated with 40-80 µM of compound DC-51-W4, when compared to DMSO control (C) ($p>0.05$) (FIGS. 1A & 5A-B of the priority application (U.S. Pat. No. 8,455,867)). A 63-85% reduction in levels of soluble TauRD oligomers, and a 49-95% reduction in levels of soluble TauRD monomers was found in cells treated with 40-80 µM, and 10-80 µM of compound DC-51-W4, respectively, when compared to DMSO control (C) ($p<0.01$)(FIGS. 2A & 5C-D of the priority application (U.S. Pat. No. 8,455,867)). In addition, with treatment of 40-80 µM of compound DC-51-W4, significant cell toxicity was also observed, as indicated by reduced cell viability (data not shown), and reduced α-tubulin levels (an indicator of total protein levels) (FIG. 2B of the priority application (U.S. Pat. No. 8,455,867)). The results suggest that compound DC-51-W4 may be toxic when used at >40 µM under the current experimental conditions.

In conclusion, the compounds of this invention modulate tau aggregation and thus potentially are suitable for alleviating tauopathies.

We claim:
1. A compound selected from the group consisting of

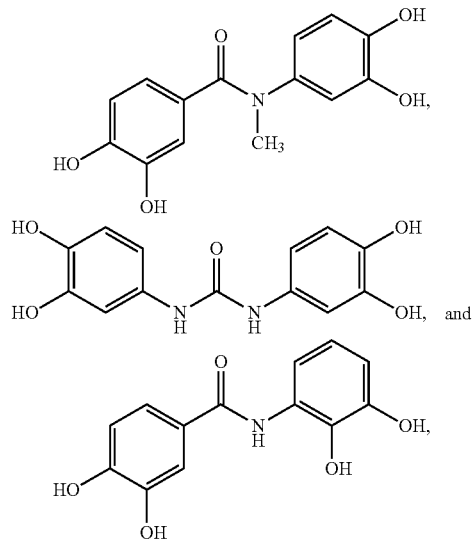

or a pharmaceutically acceptable salt thereof.

2. A method of disrupting or causing the dissolution of tau aggregates in a mammal suffering from a tauopathy, comprising administering to the mammal suffering from a tauopathy a therapeutically effective amount of a compound selected from the group consisting of

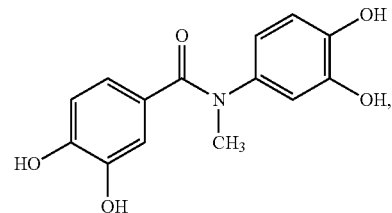

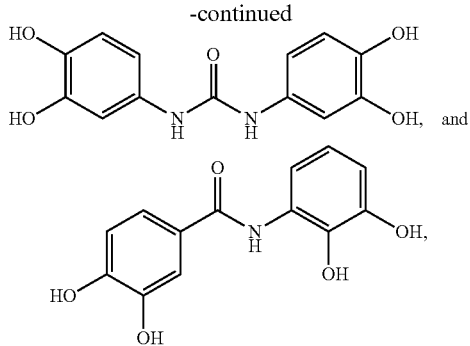

or a pharmaceutically acceptable salt thereof.

3. The method of claim 2, wherein the mammal is a human.

4. The method of claim 2, wherein the amount of the compound administered is between 0.1 mg/Kg/day and 1000 mg/Kg/day.

5. The method of claim 2, wherein the amount of compound administered is between 1 mg/Kg/day and 100 mg/Kg/day.

6. The method of claim 2, wherein the amount of compound administered is between 10 mg/Kg/day and 100 mg/Kg/day.

7. The method of claim 2, wherein the tauopathy is selected from the group consisting of Alzheimer's disease, Pick's disease, progressive supranuclear palsy, corticobasal degeneration, familial frontotemporal dementia/Parkinsonism linked to chromosome 17, amyotrophic lateral sclerosis/Parkinsonism-dementia complex, argyrophilic grain dementia, dementia pugilistic, diffuse neurofibrillary tangles with calcification, progressive subcortical gliosis and tangle only dementia.

8. The method of claim 2, wherein the compound administered is administered by one of routes selected from, oral, topical, systemic or parenteral.

* * * * *